United States Patent [19]

Logothetis et al.

[11] Patent Number: 5,089,113
[45] Date of Patent: Feb. 18, 1992

[54] MEASUREMENT AND CONTROL OF EXHAUST GAS RECIRCULATION WITH AN OXYGEN PUMPING DEVICE

[75] Inventors: Eleftherios M. Logothetis, Birmingham; Richard E. Soltis, Redford, both of Mich.

[73] Assignee: Ford Motor Company, Dearborn, Mich.

[21] Appl. No.: 670,632

[22] Filed: Mar. 18, 1991

Related U.S. Application Data

[62] Division of Ser. No. 443,537, Nov. 30, 1989, Pat. No. 5,010,762, which is a division of Ser. No. 222,864, Jul. 22, 1988, Pat. No. 4,909,072.

[51] Int. Cl.$^5$ ............................................. G01N 27/26
[52] U.S. Cl. .................................... 204/425; 73/116
[58] Field of Search ........................... 204/425; 73/116

[56] References Cited

U.S. PATENT DOCUMENTS

| | | | |
|---|---|---|---|
| 4,272,329 | 6/1981 | Hetrick et al. | 204/1 T |
| 4,272,330 | 6/1981 | Hetrick | 204/1 T |
| 4,272,331 | 6/1981 | Hetrick | 204/1 T |
| 4,300,991 | 11/1981 | Chiba et al. | 204/425 |
| 4,302,312 | 11/1981 | Ishitani et al. | 204/425 |
| 4,450,065 | 5/1984 | Yamada et al. | 204/425 |
| 4,487,680 | 12/1984 | Logothetis et al. | 204/426 |
| 4,498,968 | 2/1985 | Yamada et al. | 204/412 |
| 4,547,281 | 10/1985 | Wang et al. | 204/424 |
| 4,568,443 | 2/1986 | Asayama et al. | 204/410 |
| 4,578,172 | 3/1981 | Yamada et al. | 204/412 |
| 4,614,175 | 9/1981 | Asayama | 123/571 |
| 4,645,572 | 2/1987 | Nishizawa et al. | 204/1 T |
| 4,658,790 | 4/1987 | Kitahara | 123/440 |
| 4,675,880 | 8/1988 | Hayakawa et al. | 204/426 |
| 4,765,580 | 8/1988 | Hayakawa et al. | 204/426 |
| 4,769,124 | 9/1988 | Okada et al. | 204/426 |

OTHER PUBLICATIONS

"Closed Loop Control of the EGR Rate Using the Oxygen Sensor", M. Nishida et al., SAE International Congress and Exposition, Feb. 29–Mar. 4, 1988, Technical Paper No. 550133.

"High Temperature Oxygen Sensors Based on Electrochemical Oxygen Pumping", E. M. Logothetis and R. E. Hetrick, Fundamentals and Applications of Chemical Sensors, 1986, American Chemical Society.

*Primary Examiner*—John Niebling
*Assistant Examiner*—Bruce F. Bell
*Attorney, Agent, or Firm*—Lorraine S. Melotik; Roger L. May

[57] ABSTRACT

An electrochemical device and method measures the percentage of exhaust gas in the intake air/exhaust gas mixture going to the cylinders of an internal combustion engine. Two electrochemical pump cells and a support structure form a restricted volume in communication through an aperture to an ambient of intake air and exhaust gas mixture. Constant current is passed through a first pump cell to cause a portion of oxygen molecules inside the restricted volume to be pumped out. A constant voltage across the second pump cell causes substantially all the remaining $O_2$ molecules inside the restricted volume to be pumped out. Current flowing in the second pump cell is measured, the current being proportional to the percentage of $O_2$ inside the restricted volume and hence proportional to the percentage of $O_2$ in the intake air and exhaust gas mixture, which is a measure of % EGR.

8 Claims, 4 Drawing Sheets

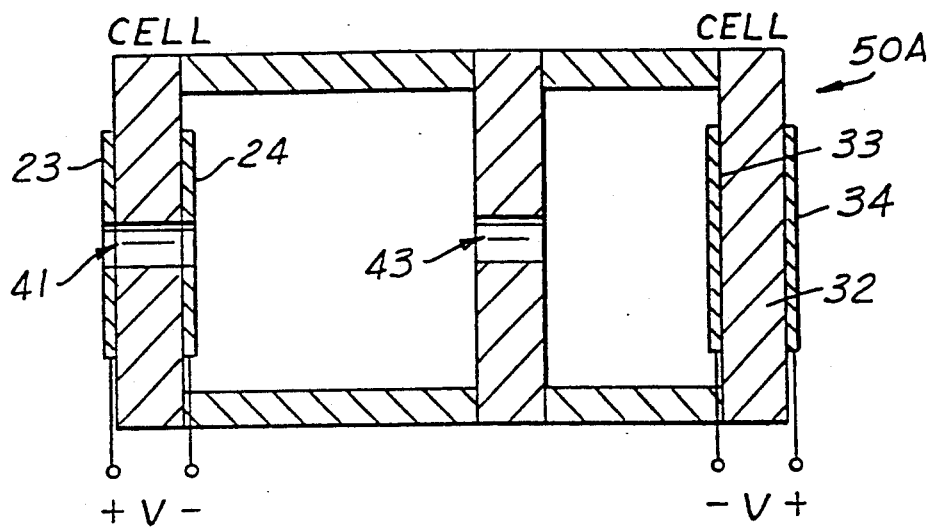
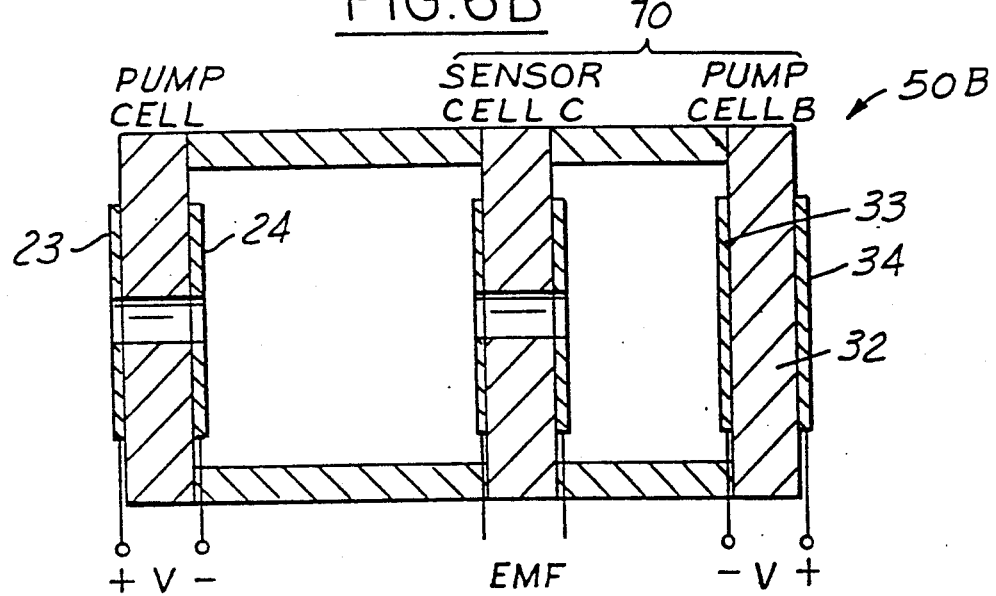
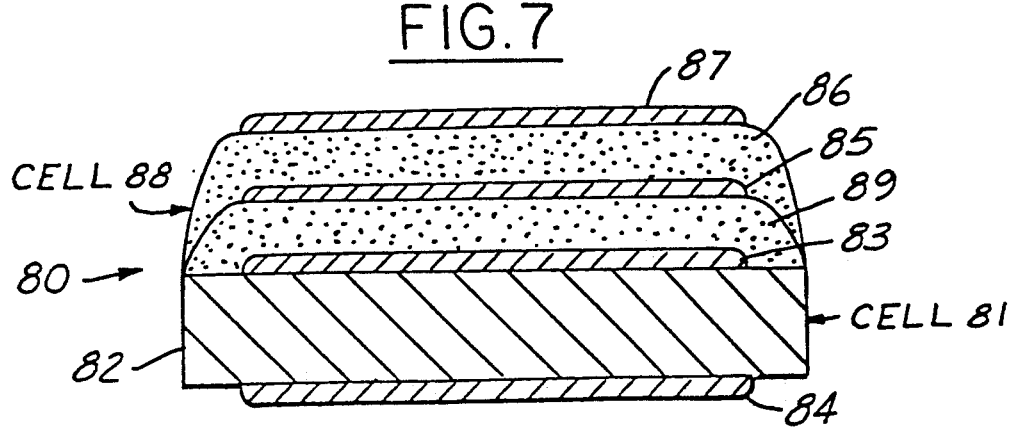

MEASUREMENT AND CONTROL OF EXHAUST GAS RECIRCULATION WITH AN OXYGEN PUMPING DEVICE

This application is a division of application Ser. No. 07/443537, filed Nov. 30, 1989, entitled MEASUREMENT AND CONTROL OF EXHAUST GAS RECIRCULATION WITH AN OXYGEN PUMPING DEVICE, which is a divisional application of application Ser. No. 07/222,864, filed July 22, 1988 entitled: MEASUREMENT AND CONTROL OF EXHAUST GAS RECIRCULATION WITH AN OXYGEN PUMPING DEVICE, which is U.S. Pat. No. 4,909,072.

Reference is made to commonly assigned and related U.S. application Ser. No. 55,821 to Logothetis et al filed May 29, 1987 and entitled "Exhaust Gas Recirculation Sensor and Method".

FIELD OF THE INVENTION

This invention relates to determining the amount of exhaust gas that is added to the intake air going to the cylinders of an internal combustion engine.

BACKGROUND OF THE INVENTION

Exhaust gas recirculation (EGR) is commonly used in vehicles with internal combustion engines to reduce the amount of $NO_x$ produced in the engine cylinders during combustion. Depending on engine operating conditions, a certain amount of exhaust gas is added through an EGR valve to the intake air that goes to the cylinders. The dilution of the intake air charge with exhaust gas results in a lower combustion temperature and thus production of smaller amounts of $NO_x$. EGR is usually measured as percentage of exhaust gas in the combined air and exhaust intake mixture. The amount of EGR is determined by the degree of opening of the EGR valve and the difference in gas pressure across the valve. Usually, EGR is measured with a position sensor that measures the degree of opening of the EGR valve. This type of measurement is not reliable, however, because a) deposits can partially block the valve and b) changes in back pressure result in changes in the amount of EGR. Another method of determining EGR is based on the measurement of the flow of the exhaust gas added to the intake air. This is done by measuring with two pressure sensors the pressure drop across an orifice through which the recirculated exhaust gas is passed. This method of determining EGR also has problems because the orifice can be partially blocked by deposits.

Still another method which may be used for measuring EGR is based on the measurement of the amount of $O_2$ in the combined (intake air and EGR) mixture. For an engine controlled at the stoichiometric air-to-fuel ratio, the percentages of $O_2$ in the exhaust gas is essentially zero. The percentage of $O_2$ in the (intake air + EGR) mixture depends on the amount of EGR as shown in FIG. 1 and can be used as a measure of EGR. The effect of humidity in the air is indicated by showing plots for 0% and 100% humidity at a temperature of 70° F. As shown, the error due to humidity decreases as the percentage of EGR increases. Correction for the error due to humidity is accomplished by measuring the percentage of $O_2$ at zero EGR (completely closed EGR valve).

In the last 20 years, several different types of oxygen sensors based on $O_2$-pumping $ZrO_2$ cells have been developed. Such oxygen-pumping is based on the fact that if a current is passed through an oxygen ion-conducting electrolyte (e.g., zirconia), oxygen is transferred (pumped) from one side of the electrolyte to the other. Such sensors have the common characteristic that their signal output is linearly proportional to the ambient oxygen partial pressure. As discussed, e.g., in "High Temperature Oxygen Sensors Based on Electrochemical Oxygen Pumping", E. M. Logothetis and R. E. Hetrick, *Fundamentals and Applications of Chemical Sensors*, 1986, American Chemical Society, the sensors may be of the single or double cell type.

In single-cell sensors, the same $ZrO_2$ cell is used for both, oxygen pumping and sensing. In double-cell sensors, different $ZrO_2$ cells are used for oxygen pumping and sensing. U.S. Pat. No. 4,547,281 to Wang is directed to a single cell device capable of sensing the concentration of oxygen in a volume. Double cell sensors are disclosed, e.g., in U.S. Pat. Nos. 4,272,329, 4,272,330, and 4,272,331 to Hetrick and Hetrick et al; 4,498,968 to Yamada et al; 4,645,572 to Nishizawa et al; and 4,487,680 to Logothetis et al. The Hetrick, Hetrick et al and Logothetis et al patents are commonly assigned with this invention. In general, in these two cell devices, one cell is used to pump a certain (variable) amount of $O_2$ out of a cavity formed between the cells and the second cell (the sensor cell) is used to measure the reduced partial pressure of $O_2$ inside the cavity. As described in the patent to Logothetis et al, the structure of that device has been modified to eliminate the cavity and employs only three electrodes, instead of the common four, but operates analogously to those of the '329, '330 and '331 patents discussed above.

Embodiments of our device are similar to the two cell devices in that they comprise two $ZrO_2$ cells, which cells may define a cavity between them or be similar to the Logothetis et al structure discussed above. Our device, however, does not use one cell for oxygen-pumping and the second for oxygen-sensing as in the two cell devices described above. Rather, our invention uses both cells as $O_2$-pumping cells.

In general, measuring changes in the $O_2$ concentration in an intake air/exhaust gas mixture is not trivial because the change in $O_2$ concentration with changes in %EGR is relatively small. Of the various types of oxygen sensors, the ones based on oxygen pumping are more appropriate because they have high sensitivity to $O_2$, weak temperature dependence and weak or no dependence on absolute gas pressure. In "Closed Loop Control of the EGR Rate Using the Oxygen Sensor", SAE International Congress and Exposition, Feb. 29--Mar. 4, 1988, Technical Paper No. 880133, M. Hishida, N. Inoue, H. Suzuki, and S. Kumargai disclose a device comprising an oxygen pump cell and a sensor cell useful to measure %EGR. For measuring small changes in $O_2$ at high $O_2$ concentrations, however, an $O_2$ sensor with higher sensitivity is desirable. The present invention describes a method for measuring EGR and an EGR sensor which overcomes this problem.

SUMMARY OF THE INVENTION

This invention provides a method for measuring the percentage of EGR by measuring the percentage of $O_2$ in the intake air exhaust gas mixture (herein taken to mean "the mixture of intake air and exhaust gas") with an electrochemical device, which $O_2$ concentration is proportional to the percentage of EGR. The method comprises restricting communication between an ambient of an intake air and exhaust gas mixture and a restricted volume and passing a constant current through a first electrochemical pump cell so that an electrode, of the first pump cell, inside the restricted volume is biased negatively causing a portion of the oxygen molecules inside the volume to be pumped out by the current flowing through the first pump cell. The method further comprises applying a constant voltage across a second electrochemical pump cell so that an electrode, of the second pump cell, inside the restricted volume is biased negatively, the constant voltage across the second pump cell being sufficient to cause substantially all of the remainder of the oxygen molecules inside the restricted volume to be pumped out by a current flowing through the second pump cell but less than that capable of disassociating $CO_2$ or $H_2O$ molecules. The method also comprises measuring a current flowing through the second pump cell, the second pump cell current being proportional to the percentage of $O_2$ molecules inside the restricted volume not pumped out by the first pump cell and also proportional to the percentage of $O_2$ molecules in the intake air and exhaust gas mixture. This invention is particularly advantageous for use in measuring the $O_2$ concentration in high-$O_2$ mixtures. Correction for variable humidity in air is accomplished by measuring the percentage of $O_2$ when the EGR valve is closed (0% EGR).

According to another aspect of this invention, an electrochemical device for measuring EGR includes a first solid electrochemical pump cell having a first pair of opposed electrodes and a second solid electrochemical pump cell having a second pair of opposed electrodes. A supporting structure is coupled to the first and second pump cells to form with them a restricted volume. This volume communicates with the ambient atmosphere (the intake air and exhaust gas mixture when used in the method of the invention) through an aperture or collection of apertures. In operation according to the method of the invention, a constant current is passed through the first pump cell (by a first external circuit means coupled to the first pump cell) so that a portion (volume %) of the oxygen molecules inside the restricted volume is pumped out. In operation, a constant voltage is applied across the second pump cell (by a second external circuit means coupled to the second pump cell) of sufficient magnitude to cause substantially all of the remainder of the $O_2$ molecules present inside the restricted volume to be pumped out and achieve a saturation current but less than that which will cause decomposition of any gas molecules containing oxygen, e.g., $CO_2$ or $H_2O$, that may be present in the restricted volume. The first external circuit means is adapted to apply an external voltage across the second pump cell which is generally less than about 0.8 volts, more preferably between about 0.2 and 0.8 volts. The saturation current of the second pump cell is proportional to the percentage of $O_2$ inside the volume, not pumped out by the first pump cell proportional to the percentage of $O_2$ in the intake air/exhaust gas mixture and to the percentage of EGR therein.

BRIEF DESCRIPTION OF THE DRAWINGS

FIGS. 6A and 6B are schematics of electrochemical devices for measuring EGR in accordance with embodiments of the present invention.

FIG. 7 is a schematic of an electrochemical device having a planar configuration for measuring EGR in accordance with an embodiment of the present invention.

DETAILED DESCRIPTION OF THE INVENTION

This invention teaches a method for determining EGR based on the measurement of the amount of $O_2$ in the intake air and EGR mixture by employing an electrochemical oxygen pumping device.

As mentioned above, several types of oxygen sensors based on oxygen pumping with $ZrO_2$ electrochemical cells exist. These sensors have several characteristics that make them suitable for lean A/F ratios (i.e., high EGR). However for measuring small changes in $O_2$ at high $O_2$ concentration, see FIG. 1, an $O_2$ sensor with higher sensitivity is desirable.

Figure 2:
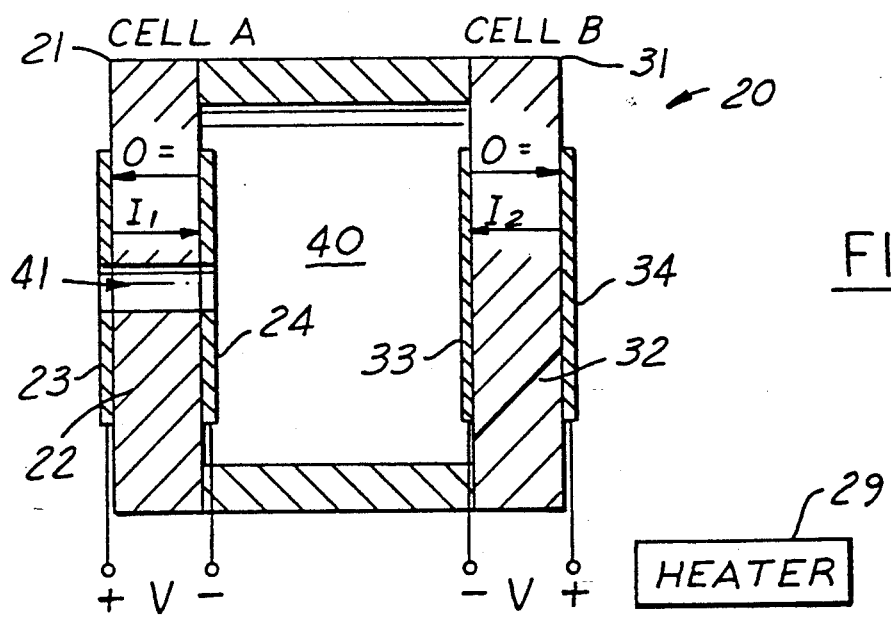
FIG. 2 is a schematic of an electrochemical device for measuring EGR according to one embodiment of this invention.

This invention measures EGR by measuring the percentage of $O_2$ in the air plus exhaust gas mixture with a sensor such as that shown in FIG. 2. This sensor 20 has two electrochemical cells 21 and 31 arranged so that a restricted volume 40 is defined. Volume 40 is linked to the ambient atmosphere (air plus EGR) through an aperture 41 or a collection of apertures. Each of the two cells consists of a platelet 22, 32 made from an oxygen conducting solid electrolyte such as $ZrO_2$, and two electrodes 23, 24; 33, 34 applied on the two sides of the platelets. These electrodes are made from platinum or some other material according to procedures well established in the area of oxygen sensors. Electrochemical cells 21 and 31 are operated as oxygen pumps by passing currents $I_1$ and $I_2$ through them. Advantageously, a heater 29 is positioned adjacent sensor 20 to provide an elevated temperature of about at least 500° C. suitable for operation of sensor 20.

Figure 3A:
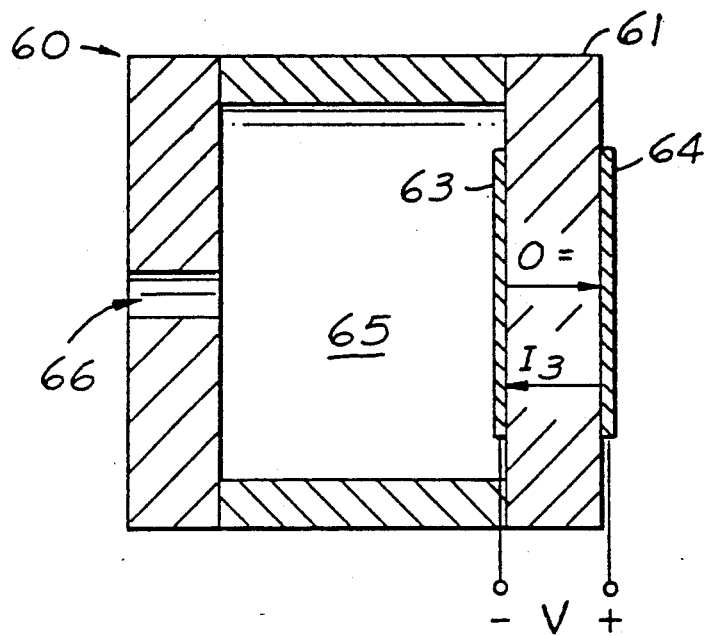
FIG. 3A is a schematic of a single-cell oxygen pumping device according to the prior art.

In order to understand the operation of device 20, first consider single $ZrO_2$ cell device 60 of FIG. 3A which is useful as a lean $O_2$-sensor. It has a single oxygen pumping cell 61 made from a $ZrO_2$ platelet with two platinum electrodes 63 and 64 arranged in a structure so that a volume 65 is defined. Volume 65 communicates with the ambient gas through an aperture 66. When a voltage is applied across cell 61 so that electrode 63 is negative, a current $I_3$ passes through the $ZrO_2$ material as a result of motion of oxygen ions from electrode 63 to electrode 64.

As the oxygen ions formed at electrode 63 travel through the $ZrO_2$ platelet to electrode 64, more $O_2$ molecules from the gas phase dissociate and react with electrons at electrode 63 to form oxygen ions ($O^=$). By means of this electrochemical reaction, as oxygen ions are depleted at electrode 63 (in traveling to electrode 64) more oxygen ions are formed from $O_2$ gas molecules in volume 65. By means of an inverse electrochemical reaction, oxygen ions at electrode 64 are released as $O_2$ molecules into the ambient gas. The net effect of the current through the cell is to pump $O_2$ out of volume 65. Because of the lower concentration of $O_2$ inside volume 65, there will be a diffusional flux of $O_2$ from the ambient (intake air plus exhaust gas mixture) into volume 65 through aperture 66. Under steady state conditions, the diffusional flux of $O_2$ into volume 65 will be equal to the flux of $O_2$ pumped out of volume 65 by the pumping current.

Figure 3B:
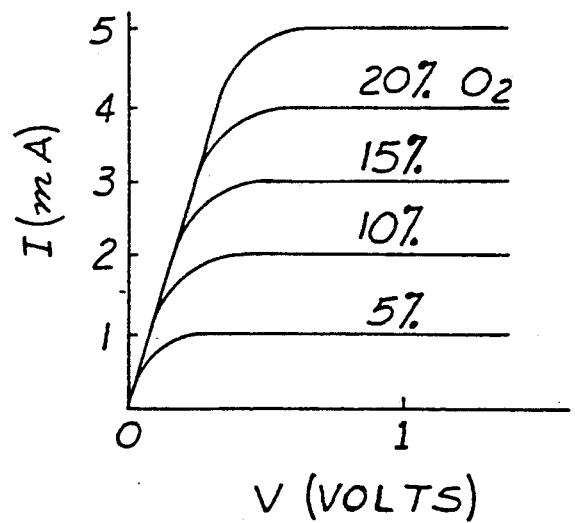
FIG. 3B is a graph relating the current voltage characteristics of the device of FIG. 3A.

If the single cell device 60 is used to measure the percentage of $O_2$ in an exhaust gas/intake air mixture, for small voltages (0.2–0.8 V) the current increases with voltage as more oxygen is pumped out of volume 65 and reaches a saturation current, $I_s$. This corresponds to the condition that all oxygen inside volume 65 is pumped out by the current. The saturation current $I_s$ is proportional to the percentage of $O_2$ in the ambient. The voltage across the pump cell is maintained below about 0.8 volts so as to not decompose any gas molecules containing $O_2$, such as $CO_2$, present in volume 65. The current voltage (I-V) characteristics of single cell prior art device 60 (for various percentages of $O_2$) under these conditions is shown in FIG. 3B.

Figure 1:
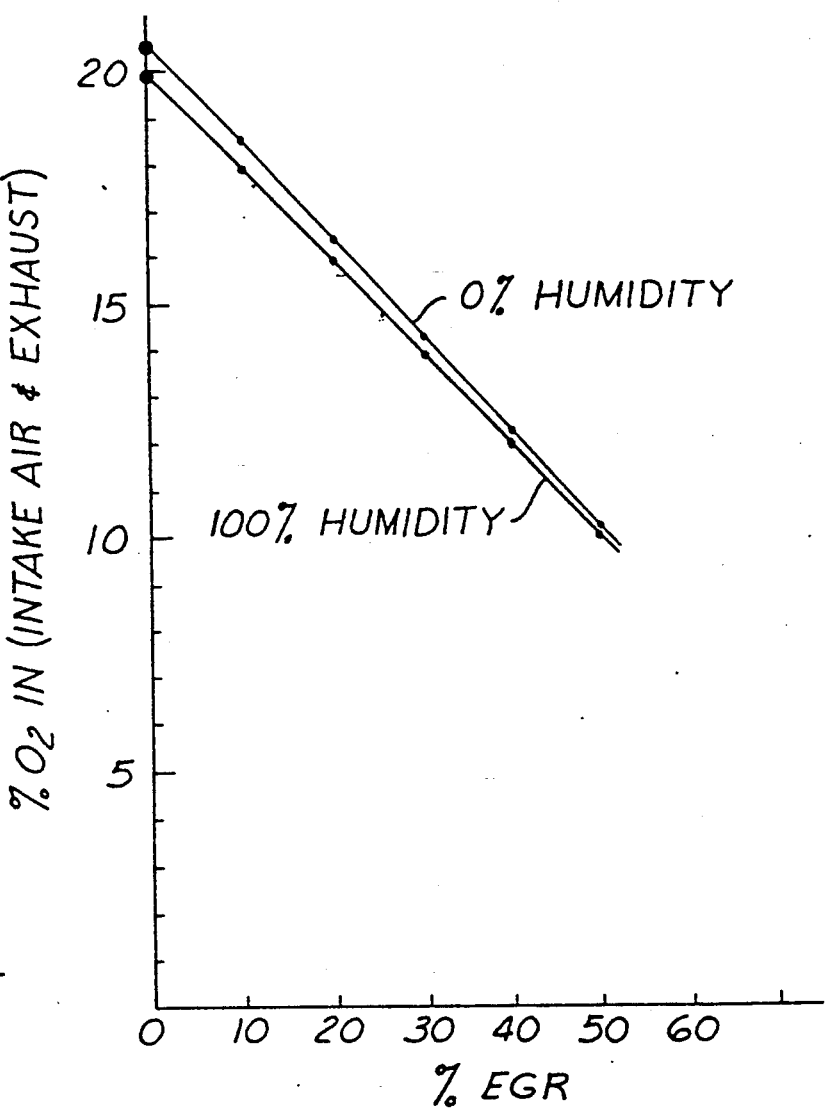
FIG. 1 is a graph relating the percentage of $O_2$ in a combined intake air and exhaust mixture to the percentage of EGR.
Figure 4:
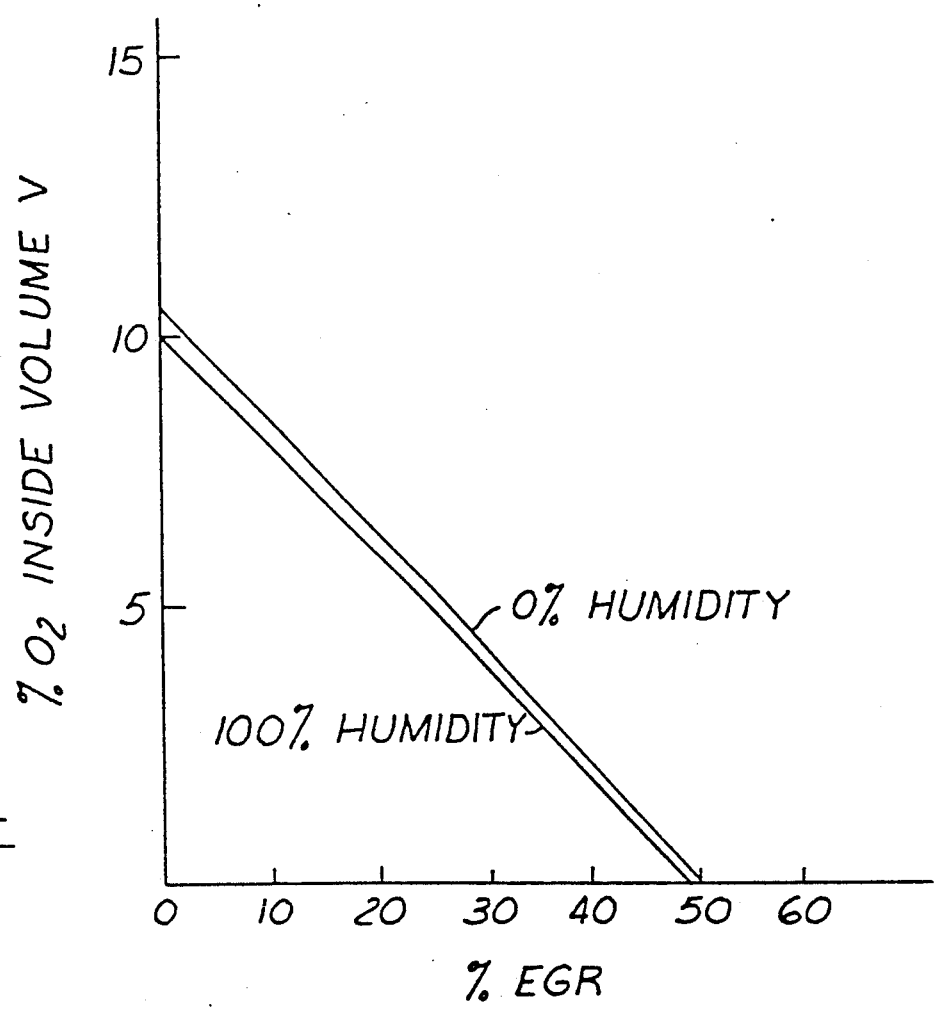
FIG. 4 is a graph relating the percentage of $O_2$ in the volume of the device of FIG. 2 as a function of the percentage of EGR.

The relationship between the percentage of $O_2$ in intake air/exhaust gas mixtures and the percentage of EGR therein is shown in FIG. 1. FIG. 4 shows the same relationship except at lower percentages of $O_2$ inside the volume. Sensitivity is generally defined as the percentage change in Y for a given change in X, as relating components from a conventional X-Y axes graph. It can be seen from FIG. 1 that for the same change in %EGR (X axis) at concentrations higher and at lower EGR (FIG. 4), there is a larger percentage change in $O_2$ (Y axis) at the higher EGR's (lower $O_2$ concentration). Thus the prior art single cell device is more sensitive to changes in EGR at low oxygen concentrations (high EGR) than it is at high oxygen concentrations (low EGR). Thus while device 61 of FIG. 3A can be suitably used for the measurement of EGR in a low-$O_2$ environment, it is not optimally sensitive in high $O_2$ (i.e. low EGR) environments.

The measurement of EGR in a high-$O_2$ intake air/exhaust gas mixture can be accomplished, however, with a device according to the Present invention. Referring to FIG. 2, device 20 can be used to measure the percentage of $O_2$ in such a gas mixture. The device comprises a first and a second oxygen pump cell. The first oxygen pumping cell pumps out a portion (e.g., 10 volume %) of the oxygen molecules from volume 40 so as to reduce the percentage of $O_2$ molecules in the gas mixture in the volume. This, in effect, modifies the percentage of $O_2$ molecules in the high $O_2$ (20–10%) intake air/exhaust gas mixture of FIG. 1 to the lower $O_2$ (10–0%) mixture of that of FIG. 4. The portion of oxygen molecules is pumped out of volume 40 by passing a constant current through cell 21 so that electrode 24 is negative. The current passed through cell 21 is that which is sufficient to cause cell 21 to pump the desired amount (portion) of the $O_2$ molecules out of volume 40. Preferably, the amount of $O_2$ pumped out of volume 40 by the first oxygen pump cell 21 equals the percentage of $O_2$ (by volume) present in the intake air multiplied by (100 minus at the maximum percentage of EGR employed by that particular internal combustion engine). Thus, removing 10 volume % of the $O_2$ as in the embodiment above would be optimal for an engine in which the maximum amount of EGR generally employed in the engine gas mixture is 50% by volume. In an engine in which the maximum amount of EGR generally employed in the engine gas mixture is 30% by volume, 14 volume % (i.e. 70 multiplied by 20%)cell 21 of the device would optimally remove of the $O_2$ molecules, leaving about 6 volume % (i.e., 30 times 20%) of the $O_2$ molecules in volume 40 at zero EGR. The current necessary to remove the desired portion of $O_2$ molecules from the volume would depend on such factors as the type and dimensions of aperture 41, and temperature. Selection of the optimum current necessary to pump the desired portion of the $O_2$ molecules out of volume 40 by means of cell 21 will be apparent to those skilled in the art in view of the present disclosure.

According to the embodiment of the invention device of FIG. 2, the percentage of $O_2$ in the reduced oxygen mixture inside volume 40 is measured by the second oxygen pump cell 31. A constant voltage of less than 0.8 volts, generally between 0.2 and 0.8 volts, is applied across the second oxygen pump cell 31 of the invention device of FIG. 2, with electrode 33 being negatively biased, to pump out substantially the remainder of $O_2$ molecules inside volume 40. The voltage across the pump cell is maintained below about 0.8 volts so as to not decompose any gas molecules containing $O_2$, such as $CO_2$, present in volume 40. For sufficiently large voltages, about 0.5 to 0.8 volts, a saturation current is achieved in cell 31. An external circuit means coupled to pump cell 31 is used to measure the saturation current flowing through the second pump cell 31. This saturation current, $I_s$, is a measure of the percentage of $O_2$ molecules in the volume 40 not pumped out by first pump cell 21 and also is proportional to the percentage of $O_2$ molecules in the intake air and exhaust gas mixture.

In effect, the reduced-$O_2$ mixture inside volume 40 (effected by the pumping out of a portion of the $O_2$ molecules from volume 40 by cell 21) simulates a low-$O_2$ mixture. This allows the device to measure the percentage of $O_2$ in a high-$O_2$ mixture with the sensitivity obtained when measuring low-$O_2$ mixtures. Thus the device of this invention provides a more sensitive measurement of EGR in a high-$O_2$ intake air/exhaust gas mixture as compared to that obtained by the single $O_2$ pumping prior art device 3A.

Figure 5:
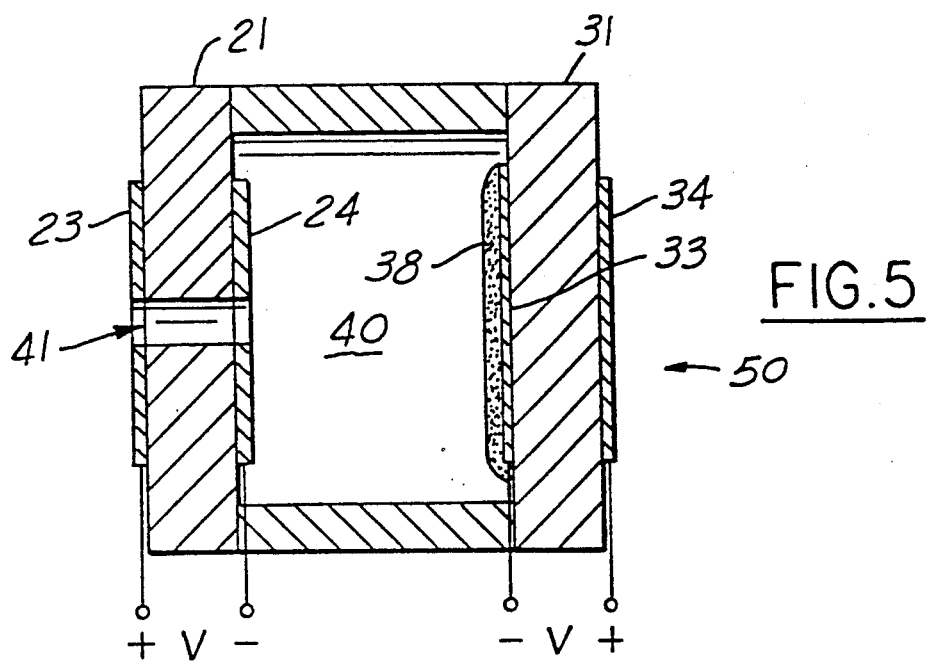
FIG. 5 is a schematic of an electrochemical device for measuring the EGR according to a second embodiment of the present invention.

The device of FIG. 2 operates under the assumption that cell 21 can pump the desired portion of oxygen entering volume 40 through aperture 41 so that only the remainder of the $O_2$ reaches cell 31. If this is not the case with the device structure of FIG. 2, the desired condition can be accomplished by modifying its structure to that of device 50 as shown in FIG. 5. In this structure, a porous layer 38 is deposited on top of the inner electrode of cell 31. This porous layer is made from $ZrO_2$ or an inert material (e.g. spinel or aluminum oxide) and acts as a hindrance (barrier) to $O_2$ diffusion so that the desired portion of $O_2$ is pumped out by cell 21.

Several other device configurations are possible. According to other embodiments of this invention, the two pumping cells are more strongly decoupled by placing between them barriers to oxygen diffusion. For example, the porous layer in the device of FIG. 5 may be replaced with a "wall" 42 having an aperture 43 as shown in device 50A of FIG. 6A. Another type of configuration is shown in device 50B of FIG. 6B. Device 50B uses a pump cell to remove a portion of the $O_2$ and a pump cell/sensor cell structure 70 (similar to the sensor structure described in U.S. Pat. No. 4,272,329 by Hetrick et al) to remove and measure the remaining $O_2$.

The electrochemical device for the measurement of EGR disclosed here can also be made in a planar configuration. FIG. 7 shows one embodiment of a planar device 80 according to this invention. One starts with a dense $ZrO_2$ platelet 82 and deposits porous platinum electrodes 83 and 84 on both sides of platelet 82 to form pump cell 81. A porous layer 89 made of $ZrO_2$ or an inert material (e.g. spinel or aluminum oxide) is deposited on top of platinum electrode 83 to form a barrier to diffusion of $O_2$ molecules. A porous platinum electrode 85 is deposited on layer 89 followed by another porous layer 86 of $ZrO_2$ Finally, a porous platinum electrode 87 is deposited on top of layer 86. Porous $ZrO_2$ layer 86 and platinum electrodes 85 and 87 form pump cell 88. As in the case of the device of FIG. 2, a constant current is passed through pump cell 88 to pump a portion of the oxygen out of the porous parts of the structure, and a constant voltage of between about 0.2 and 0.8 volts is applied across pump cell 81 to pump out substantially all of the remaining $O_2$ inside the porous layer 89. The saturation current of pump cell 81 is proportional to the percentage of EGR in the gas mixture.

Various modifications and variations will no doubt occur to those skilled in the art to which this invention pertains. For example, the particular construction of the two cell oxygen pumping device may be varied from that disclosed herein. These and all other variations which basically rely on the teachings through which this invention has advanced the art are properly considered within the scope of this invention.

We claim:

1. An electrochemical device for measuring the percentage of exhaust gas recirculation (EGR) in an intake air and exhaust gas mixture of an internal combustion engine, said electrochemical device including:
   a generally planar first electrochemical pump cell including a relatively dense $ZrO_2$ platelet with porous platinum electrodes on two sides of said platelet;
   a first porous $ZrO_2$ layer deposited on one electrode of said first pump cell;
   a generally planar second electrochemical pump cell including a first porous platinum electrode, a second porous $ZrO_2$ layer and a second porous platinum electrode deposited successively on said first porous $ZrO_2$ layer;
   a second cell external circuit means coupled to said second pump cell for passing a constant current through said second pump cell so that said second electrode is biased positively causing a portion of the oxygen molecules inside said first porous $ZrO_2$ layer to be pumped out by said current flowing through said second pump cell;
   a first cell external circuit means coupled to said first pump cell for applying a constant voltage across said first pump cell so that the exposed electrode is biased positively, said constant voltage across said first pump cell being sufficient to cause substantially all of the remainder of the oxygen molecules inside said first porous $ZrO_2$ layer to be pumped out by a current flowing through said first porous $ZrO_2$ layer but less than that capable of disassociating $CO_2$ or $H_2O$ molecules; and
   a third external circuit means coupled to said first pump cell for measuring the current flowing through said first pump cell, said current being proportional to the percentage of $O_2$ inside said first porous $ZrO_2$ layer not pumped out by said second pump cell and also proportional to the percentage of $O_2$ in said intake air and exhaust gas mixture.

2. The electrochemical device as recited in claim 1, further comprising a heater to maintain the temperature of said device at least about 500° C.

3. The electrochemical device as recited in claim 1, wherein the percentage of oxygen molecules pumped out of said first porous $ZrO_2$ layer by said second pump cell equals the percentage of oxygen present in said intake air and exhaust gas mixture of said engine at maximum exhaust gas recirculation.

4. The electrochemical device as recited in claim 1, wherein said first external circuit means is adapted to apply across said first pump cell a constant voltage in the range 0.2 to 0.8 volts.

5. A method for measuring the percentage of exhaust gas recirculation in an intake air and exhaust gas mixture of an internal combustion engine including the steps of:
   forming a generally planar first electrochemical pump cell including a relatively dense $ZrO_2$ platelet with porous platinum electrodes on two sides of said platelet;
   depositing a first porous $ZrO_2$ layer on top of one of the electrodes of said pump cell;
   forming a generally planar second electrochemical pump cell including a porous platinum electrode, a second porous $ZrO_2$ layer and a porous platinum electrode deposited successively on top of said first porous $ZrO_2$ layer;
   passing a constant current through said second pump cell so that the exposed electrode is biased positively causing a portion of oxygen molecules inside said first porous $ZrO_2$ layer to be pumped out by the current flowing through said second pump cell;
   applying a constant voltage across said first pump cell so that the exposed electrode is biased positively, said constant voltage across said first pump cell being sufficient to cause substantially all of the remainder of the oxygen molecules inside said first porous $ZrO_2$ layer to be pumped out by a current flowing through said first porous $ZrO_2$ layer but less than that capable of disassociating $CO_2$ or $H_2O$ molecules; and
   measuring the current flowing through said first pump cell, said current being proportional to the percentage of $O_2$ inside said first porous $ZrO_2$ layer not pumped out by second pump cell and also proportional to the percentage of $O_2$ in said combined intake air and exhaust gas mixture.

6. A method for measuring exhaust gas recirculation as recited in claim 5, wherein the variability of the humidity in the air is corrected by additionally measuring the percentage of $O_2$ in the intake air and exhaust gas mixture when an exhaust gas recirculation valve is closed thereby stopping exhaust gas recirculation.

7. The method for measuring exhaust gas recirculation as recited in claim 5, wherein the percentage of oxygen pumped out of said first porous $ZrO_2$ layer equals the percentage of oxygen present in said intake air and exhaust gas mixture of said engine at maximum exhaust gas recirculation.

8. The method for measuring exhaust gas recirculation as recited in claim 5, wherein said constant voltage applied across said first pump cell is in the range 0.2 to 0.8 volts.

* * * * *